US00PP13502P2

(12) United States Plant Patent
Zaiger et al.

(10) Patent No.: US PP13,502 P2
(45) Date of Patent: Jan. 21, 2003

(54) INTERSPECIFIC TREE NAMED 'FLAVOR JEWEL'

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 10/046,035

(22) Filed: Jan. 15, 2002

(51) Int. Cl.[7] ..... A01H 5/00
(52) U.S. Cl. ..... Plt./180
(58) Field of Search ..... Plt./180

*Primary Examiner*—Bruce R. Campell
*Assistant Examiner*—Anne Marie Grünberg

(57) ABSTRACT

A new and distinct variety of interspecific tree. The following features of the 6 year old tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consists of the following combination of desirable features:

1. Heavy and regular fruit production in the late maturity season.
2. Fruit with an attractive red skin color.
3. Fruit with firm flesh, having very good storage and shipping quality.
4. Fruit with very good flavor and eating quality.
5. Vigorous, upright growth habit.
6. Fruit with high Brix of 18.3°, with good balance between acid and sugar.

1 Drawing Sheet

STATEMENT REGARDING FEDERALLY SPONSORED RESEARCH OR DEVELOPMENT

Not applicable.

BACKGROUND OF THE VARIETY

Field of the Invention

In the field of plant genetics, we conduct an extensive and continuing plant-breeding program including the organization and asexual reproduction of orchard trees, and of which almonds, apples, pears, plums, peaches, nectarines, apricots, cherries and interspecifics are exemplary. It was against this background of our activities that the present variety of interspecific tree [(*Prunus salicina*×(*Prunus salicina*×*Prunus armeniaca*))×*Prunus salicina*] was originated and asexually reproduced by us in our experimental orchard located near Modesto, Stanislaus County, Calif.

Prior Varieties

Among the existing varieties of plum trees which are known to us, and mentioned herein, are 'Friar' Plum (non-patented), 'King David' Plum (non-patented), 'Mariposa' Plum (U.S. Plant Pat. No. 2,111), 'Ebony' Plum (U.S. Plant Pat. No. 2,049) and 'Red Beaut' Plum (U.S. Plant Pat. No. 2,539).

ORIGIN OF THE VARIETY

The present new variety of interspecific tree [(*Prunus salicina*×(*Prunus salicina*×*Prunus armeniaca*))×*Prunus salicina*], was originated by us in our experimental orchard, located near Modesto, Calif., as a seedling from an open pollinated interspecific seedling which originated from a first generation cross between proprietary lines of the immediate parents with the field identification numbers 48ED292 and 105GD55. The maternal parent 48ED292 originated from an open pollinated seedling of 'King David' Plum (non-patented) crossed with a plumcot derived from a 'Red Beaut' Plum (U.S. Plant Pat. No. 2,539) crossed with an apricot of unknown parentage. The pollen parent 105GD55 derived as a seedling from crosses between the plum parents 'Friar' Plum (non-patented), 'Mariposa' Plum (U.S. Plant Pat. No. 2,111) and 'Ebony' Plum (U.S. Plant Pat. No. 2,049). We planted and grew a large number of these seedlings on their own root system and, under close and careful observation, we recognized the desirable fruit characteristics of the present variety and, in 1995, selected it for asexual propagation and commercialization.

ASEXUAL REPRODUCTION OF THE VARIETY

Asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present variety of interspecific tree [(*Prunus salicina*×(*Prunus salicina*×*Prunus armeniaca*))×*Prunus salicina*] is of large size, vigorous, upright growth and a regular bearer of large, firm, late maturing fruit with very good flavor and eating quality. The fruit is further characterized by holding firm on the tree 7 to 10 days after maturity, being relatively uniform in size throughout the tree and having excellent storage and shipping quality, having an attractive red skin color and having high soluble solids of 18.3° Brix. In comparison to 'Friar' Plum (non-patented), the new variety is cordate in shape with red skin color, compared to an oblate shape, with blue black skin color and the new variety is approximately 2 weeks later in maturity.

In comparison to the 'Ebony' Plum (U.S. Plant Pat. No. 2,049), the new variety is cordate in shape compared to a round shape and is red in skin color compared to a deep purple blue color.

PHOTOGRAPH OF THE VARIETY

The accompanying color photographic illustration shows typical specimens of the foliage and fruit of the present new interspecific variety. The illustration shows the upper and lower surface of the leaves, an exterior and sectional view of a fruit divided in its suture plane to show flesh color, pit cavity and the stone remaining in place. The photographic illustration was taken shortly after being picked (shipping ripe) and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color.

Tree:

*Size.*—Large, normal for commercial interspecific tree varieties. Usually pruned to 3 to 3.5 meters in height and width for economical harvesting of fruit.

*Vigor.*—Vigorous. Growth of 1.5 to 2 meters in height the first growing season. Varies with fertility of soil, climatic conditions and cultural practices.

*Form.*—Upright. Usually pruned to vase shape to increase sunlight to center of tree.

*Branching habit.*—Upright. Crotch angle approximately 25°. As tree matures, crop load increases crotch angle.

*Productivity.*—Productive. Usually set ½ to more times fruit desired. Thinning and spacing of fruit required.

*Bearer.*—Regular. Has had adequate fruit set 4 consecutive years. No alternate bearing observed.

*Fertility.*—Self-sterile, pollenizer required.

*Density.*—Medium dense. Usually center branches are removed to create a vase shape to allow more sunlight to center of tree to enhance fruit color, Brix and health of fruit bearing wood.

*Hardiness.*—Hardy in all stone fruit growing areas of California. Approximate winter chill of 800 hours at or below 45° F.

Trunk:

*Size.*—Medium to large. Average circumference 45.7 cm at 24.1 cm above ground.

*Stocky.*—Medium.

*Surface.*—Medium shaggy, roughness increases with age of tree.

*Color.*—5Y 4/2 to 5Y 6/2.

Branches:

*Size.*—Medium to large. Average circumference 16.4 cm at 1.5 meters from ground.

*Surface texture.*—New growth smooth. Mature growth medium rough, roughness increases with age of branch.

*Lenticels.*—Numerous, average 89 in a 25.8 square cm surface. Average length 4 mm. Average width 1.3 mm. Color 2.5YR 6/12.

*Color.*—New growth 2.5GY 7/8 to 2.5GY 6/8. Old growth 5YR 3/4 to 5YR 4/4, varies with age of growth.

Leaves:

*Size.*—Medium to large. Average length 119.9 mm. Average width 47.5 mm.

*Form.*—Oblanceolate, apex acuminate, base cuneate.

*Margin.*—Serrate.

*Thickness.*—Medium.

*Surface.*—Upper surface relatively smooth, slightly indented over midrib and leaf veins, glabrous. Lower surface relatively smooth, small ridges created by midrib and pinnate venation, glabrous.

*Petiole.*—Average length 15 mm. Average width 2 mm. Grooved longitudinally, glabrous. Color 5GY 9/4 to 7.5R 3/10, varies with exposure to sunlight.

*Glands.*—Reniform. Small. Average length 0.9 mm. Average width 0.4 mm. Average number 2. Color 5GY 8/6. Located on upper portion of petiole and lower portion of leaf blade.

*Color.*—Upper surface 5GY 3/6. Lower surface 5GY 5/4. Midvein color 5GY 9/4.

Flower buds:

*Size.*—Medium to large. Average length 10.1 mm. Average diameter 4.0 mm.

*Hardiness.*—Hardy in all stone fruit growing areas of California. Grown in USDA Hardiness Zone 9.

*Form.*—Conical, becomes oblong before opening.

*Pedicel.*—Average length 11.4 mm. Average width 0.6 mm. Color 2.5GY 8/6.

*Color.*—N9/0.5.

*Number of buds per spur.*—Usually 15, varies from 7 to 25.

Flowers:

*Size.*—Medium to large, showy. Average height 12.6 mm. Average diameter 19.9 mm.

*Petals.*—Number — 5, alternately arranged to sepals. Shape — orbicular, narrows at point of attachment. Average length 10.1 mm. Average width 8.9 mm. Color — N9/.5. Margin — entire, slightly cupped or clawed near apex. Both surfaces glabrous.

*Sepals.*—Number — 5, alternately arranged to petals. Shape — ovate, apex rounded. Average length 2.5 mm. Average width 2.4 mm. Both outer and inner surfaces glabrous. Color — upper surface 2.5GY 8/8. Lower surface 2.5GY 8/8.

*Stamens.*—Average of 42 per flower. Average filament length 7.5 mm. Filament color 2.5GY 9/2. Anther color 1.25Y 8/16.

*Pollen.*—Abundant, self-sterile, pollenizer required. Color — 1.25Y 8/16.

*Pistil.*—Usually 1. Average length 10.9 mm. Glabrous. Stigma approximately 2.2 mm below anthers. Color 2.5GY 9/2.

*Fragrance.*—Moderate.

*Blooming period.*—Date of First Bloom Feb. 25, 2001. Date of Petal Fall Mar. 7, 2001. Varies slightly with climatic conditions.

*Color.*—N9/0.5.

*Number of flowers per flower bud.*—Usually 2, varies from 1 to 3.

*Pedicel.*—Average length 12.4 mm. Average width 0.7 mm. Color 2.5GY 7/6.

Fruit:

*Maturity when described.*—Firm ripe.

*Date of first picking.*—Aug. 12, 2001.

*Date of last picking.*—Aug. 18, 2001. Varies slightly with climatic conditions.

*Size.*—Large. Average diameter axially 66 mm. Average transversely in suture plane 70.2 mm. Average weight 158.7 grams. Average weight varies slightly with fertility of the soil, amount of thinning and climatic conditions.

*Form.*—Cordate.

*Suture.*—Shallow, extends from base to apex.

*Ventral surface.*—Nearly smooth, only very slightly lipped.

*Apex.*—Rounded.

*Base.*—Retuse.

*Cavity.*—Rounded to slightly elongated in suture plane. Average depth 3.3 mm. Average diameter 5.6 mm.

Stem:

*Size.*—Medium. Average length 14 mm. Average diameter 1.9 mm.

*Color.*—5YR 4/6 to 5YR 3/6.

Flesh:

*Ripens.*—Evenly.

*Texture.*—Firm, meaty.

*Fibers.*—Few, small, tender.

*Firmness.*—Firm, comparable to 'Friar' Plum (non-patented), firmer than 'Mariposa', Plum (U.S. Plant Pat. No. 2,111) at same stage of maturity.

*Aroma.*—Slight.

*Amydgalin.*—Undetected.

*Eating quality.*—Very good.

*Flavor.*—Very good. Good balance between acid and sugar.

*Juice.*—Moderate amount, enhances flavor.

*Brix.*—18.3°. Varies slightly with amount of fruit per tree and climatic conditions.

*Color.*—2.5Y 8/6 to 2.5Y 8/8 toward center of fruit, darkening near skin to 7.5R 4/12 to 7.5R 4/14. Pit cavity color — 2.5YR 6/10.

Skin:

*Thickness.*—Medium, normal for commercial interspecific and plum varieties.

*Surface.*—Smooth.

*Bloom.*—Heavy, complete coverage.

*Tendency to crack.*—None.

*Color.*—Ground color 10YR 8/8 to 10YR 8/10, nearly overspread with 7.5R 5/16 to 7.5R 4/16. Very small, randomly spaced areas of ground color showing, leaving a speckling pattern to the surface in most areas of the skin.

*Tenacity.*—Tenacious to the flesh.

*Astringency.*—Undetected.

Stone:

*Type.*—Clingstone.

*Size.*—Medium to large. Average length 24 mm. Average width 17.9 mm. Average thickness 8.9 mm.

*Form.*—Ovate.

*Base.*—Rounded to flat.

*Apex.*—Acuminate. Average length varies from 1.9 mm to 2.3 mm.

*Surface.*—Very lightly pitted throughout, 3 to 4 small, narrow ridges running from base toward apex, approximately ⅓ the length of the stone. One small, shallow groove on each side of suture.

*Sides.*—Mostly equal, some unequal with one side extending further from suture plane.

*Ridges.*—Small, relatively smooth.

*Tendency to split.*—None.

*Color.*—10YR 8/6 to 10YR 7/6 , when dry.

Kernal:

*Form.*—Ovate, apex acute.

*Taste.*—Bitter.

*Viability.*—Viable. Embryo fully developed.

*Size.*—Average length 16.3 mm. Average width 10.1 mm. Average thickness 5.1 mm.

*Skin color.*—2.5Y 8/6, when dry.

Use: Dessert. Market — local and long distance.

Keeping quality: Excellent, held firm in cold storage 3 weeks at 38° to 42° F. without shriveling, internal breakdown of flesh, wooliness or loss of eating quality.

Shipping quality: Excellent, showed minimal skin scarring or flesh bruising during picking, packing or shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program.

The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

We claim:

1. A new and distinct interspecific tree, substantially as illustrated and described, characterized by its large size, vigorous, upright growth and being a productive and regular bearer of large, firm, clingstone fruit maturing in the late maturity season, with very good flavor and eating quality; and in comparison to the fruit of one of its parents 'Friar' Plum (non-patented), the new variety is cordate in shape with red skin color, compared to oblate shape with blue black skin color and is approximately 2 weeks later in maturity.

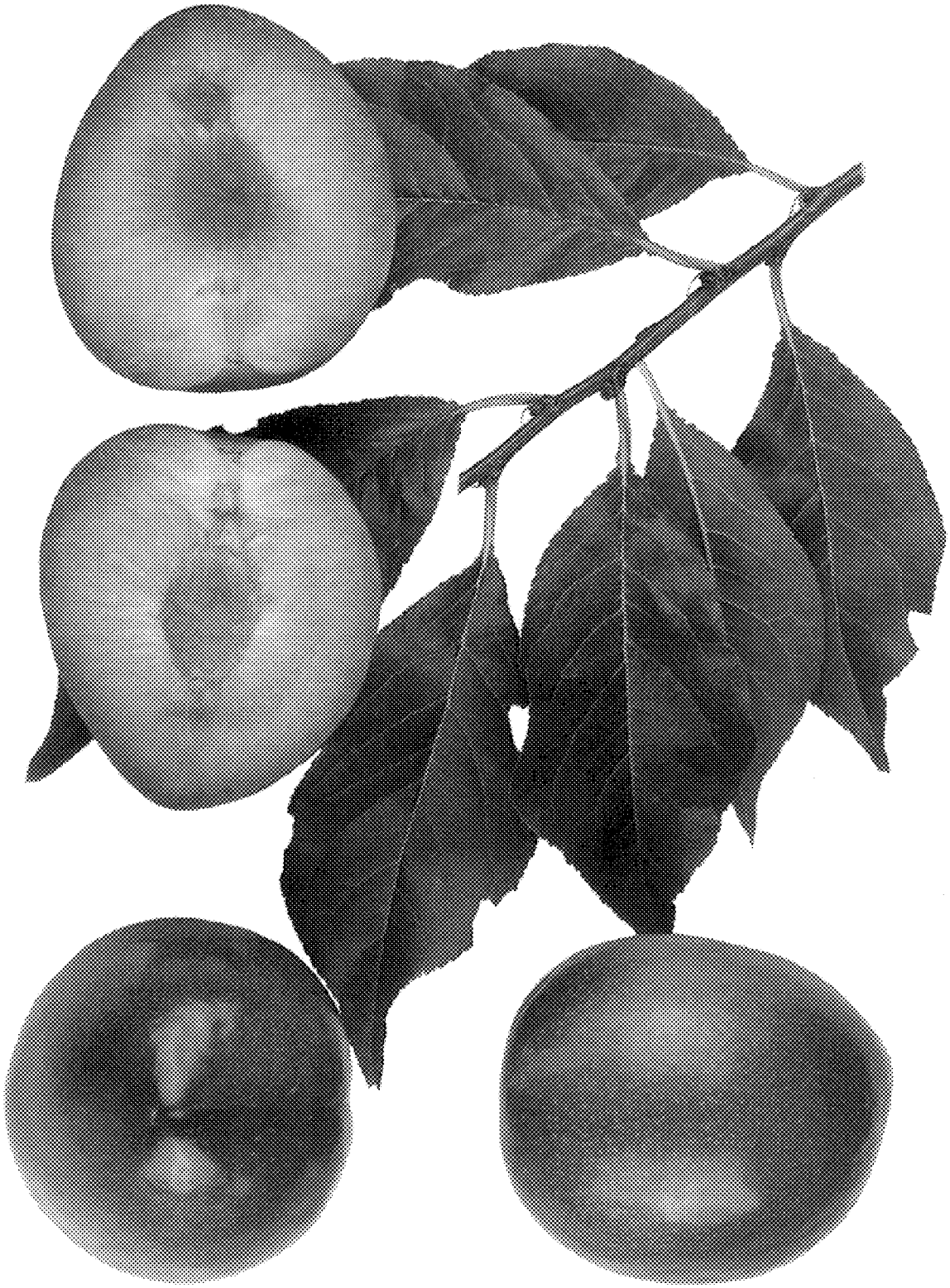

* * * * *